United States Patent [19]

Smith

[11] 4,019,503

[45] Apr. 26, 1977

[54] CRADLE ASSEMBLY

[76] Inventor: Willie R. Smith, Rte. 2, Box 255, Inverness, Fla. 32650

[22] Filed: Dec. 1, 1975

[21] Appl. No.: 636,530

[52] U.S. Cl. .................................. 128/83.5; 128/94
[51] Int. Cl.² ........................................ A61F 5/04
[58] Field of Search ............... 128/83.5, 83, 84, 94, 128/80 R, 80 G

[56] References Cited

UNITED STATES PATENTS

| | | |
|---|---|---|
| 2,607,340 | 8/1952 | Anderson .............................. 128/94 |
| 2,871,852 | 2/1959 | Miller ................................. 128/80 G |
| 2,966,905 | 1/1961 | Kamenshine ....................... 128/80 R |
| 3,739,772 | 6/1973 | Ennis ................................. 128/80 G |

*Primary Examiner*—John D. Yasko

[57] ABSTRACT

A cradle assembly including a rigid base supporting at opposite ends thereof a handle including a grasp element attached thereto and a stirrup assembly dimensioned and configured to be disposed in surrounding relation to the casted limb. A support element is integrally attached in exposed outwardly extending relationship relative to the stirrup assembly wherein relative dispositions between the support element and the stirrup assembly causes a supporting engagement between the cradle assembly and the casted limb for manipulation or orientation of the casted limb by the user thereof through manipulation of the cradle assembly. Connecting straps may serve to attach the cradle assembly to the casted limb so that it may be mounted on and moved with the casted limb if desired.

10 Claims, 4 Drawing Figures

U.S. Patent  April 26, 1977  4,019,503
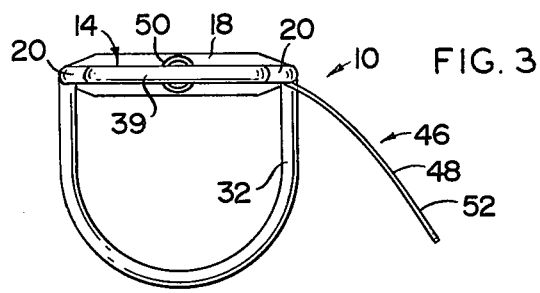
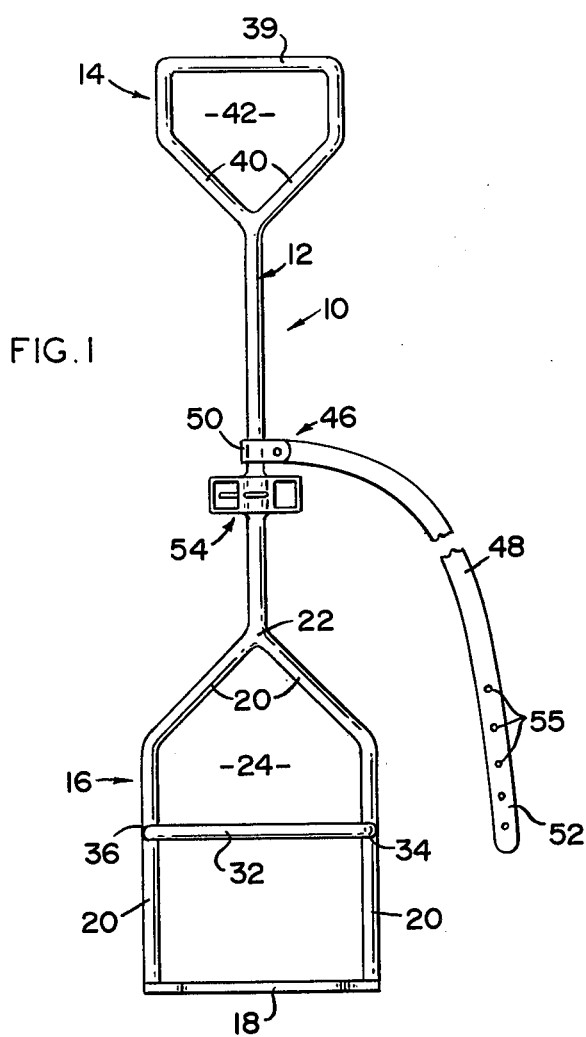
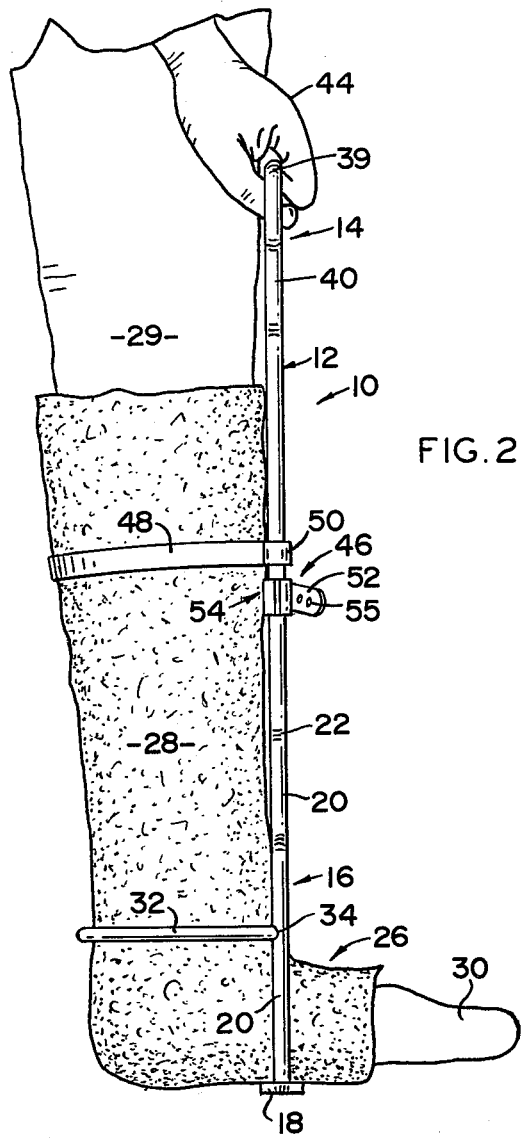
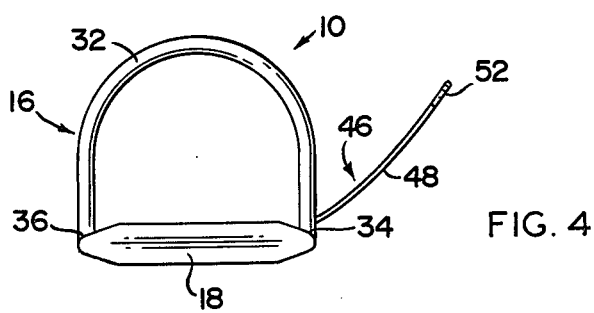

CRADLE ASSEMBLY

BACKGROUND OF THE INVENTION

1. Field of the Invention

This invention relates to a device used to manipulate a casted limb by virtue of its mounting an disposition relative thereto wherein the device is specifically configured in supporting relation relative to the casted limb.

2. Description of the Prior Art

For many years the commonly accepted treatment for broken or fractured limbs involved the use of a hard, rigid cast disposed in supporting, surrounding relation to the limb. Commonly, such casts are made from a "plaster" material which is formed about the injured limb in a fluid state and is then allowed to harden or cure into a firm, rigid "mold" in which the limb is encased. While such treatment has been found to be very effective in the healing of broken or fractured limbs, it is associated with certain disadvantages which relate generally to the comfort of the patient during the period when such cast has to be worn. Depending upon the nature of fracture and/or break and its location, such casts frequently have to cover a major portion of the leg and/or arm of the patient. When such is the case, the patient frequently encounters great difficulty in moving or manipulating the casted limb due to the weight of the cast itself and the obvious weakness of the limb due to the injury which makes the cast a necessity. Frequently, in order to even accomplish minimal movement of the casted limb, the patient requries help from another person to get in and out of bed and/or otherwise orient the casted limb to a position where the patient is relatively mobile. Obviously, this presents problems and great inconvenience to the patient when he is alone and attendants are not available to come to his aid. The inability of the patient to move the casted limb, without aid, will also frequently result in embarrassment or even danger to the patient in cases of the requirement of relieving normal body functions or in the event of an emergency, again when such attendants are not available.

Various support devices have been available in the prior art which are designed to be used in combination with a cast surrounding a limb. However, the vast majority of these devices are related to traction type structures or support structions which help to take the weight or stress off the cast itself during movement of the casted limb or the patient.

Such prior art structures are disclosed in the U.S. Pat. Nos. to Niessen, 2,146,842; Gray, 2,198,995; Hahn, 2,392,735; Ettinger, 2,427,951 and 2,547,570. Again, while all of these structures are specifically designed for use in combination with a casted limb, none are specifically intended to allow manipulation or positioning of the casted limb by the patient without the aid of attendants.

Accordingly, it can readily be seen that there is a need in the medical profession and related industries for a structure which can be readily attached to or removed from a casted limb and be supportive thereof so as to allow the patient to orient or position the casted limb without the aid of attendants.

Such a structure should be generally light weight and of simple design and configuration so as to eliminate low cost of production and/or maintenance and have an extended durable and operable life.

SUMMARY OF THE INVENTION

This invention relates to a cradle assembly of the type primarily designed and configured for supportive, removable and surrounding relation relative to a cast formed on an injured limb or the like. Supportive disposition of the cradle assembly relative to the cast is for the purpose of allowing the patient to manipulate the casted limb without the need or aid of attendants. Particularly, such cradle assembly is disposed relative to the casted limb to allow the patient to position the casted limb in the necessary location when getting on and off a bed, etc.

The cradle assembly includes a base means having a substantially elongated, rigid configuration and structure. The base means is disposed in interconnecting relation between a handle means defining one end of the cradle assembly and a stirrup means defining the substantially opposite end of the cradle assembly.

The cradle assembly includes a base plate disposed in supportive relation to one end and preferably the foot portion of the casted limb. At least two leg elements are attached to the base plate at one end and to the base means at the other wherein the leg elements are arranged in substantially spaced apart relation to define a aperture means. The aperture means is specifically configured and disposed to allow the foot portion of the casted limb to pass therethrough wherein the stirrup assembly is disposed in surrounding relation to the end or foot portion of the casted limb.

A support means is connected to the stirrup assembly in spaced relation thereto. Its disposition is such as to extend outwardly therefrom wherein the support means includes a substantially curvilinear configuration along the longitudinal axis thereof. More specifically, opposite ends of the support means are integrally attached to separate of the two leg elements on correspondingly positioned locations thereof wherein both the support means and the stirrup means are disposed in surrounding relation to the foot or end portion of the casted limb so as to allow manipulation thereof.

As set forth above, a handle means is integrally attached to the base means at the opposite end of the cradle assembly relative to the stirrup means. The handle means has an apertured configuration and a grasp element specifically designed and configured to allow the hand of the patient to grasp the handle means and thereby manipulate the entire cradle assembly by virtue of the relative disposition between the base means, the handle means and the stirrup assembly with support means attached thereto.

Connecting means in the form of one or more strap elements are attached along the length of the base means and/or the cradle assembly. These strap elements have one end attached to the base means or other portion of the cradle assembly and are of sufficient length to be disposed in surrounding relation to the casted limb. The opposite or free end of the strap element may be "buckled" into fixed engagement with the cradle assembly so that the cradle assembly may be mounted on the casted limb for movement therewith. Obviously, other means of attachment of the strap element to the base means and/or cradle assembly may be utilized such that each of the strap elements may be disposed in surrounding relation to the casted element for the purpose and reasons as set forth above.

The invention accordingly comprises the features of construction, combination of elements and arrangement of parts which will be exemplified in the construction hereinafter set forth and the scope of the invention will be indicated in the claims.

BRIEF DESCRIPTION OF THE DRAWINGS

For a fuller understanding of the nature and objects of the invention, reference should be had to the following detailed description taken in connection with the accompanying drawing in which:

FIG. 1 is a front view of the cradle assembly of the present invention with strap element attached thereto.

FIG. 2 is a side view of the cradle assembly mounted on a casted limb for movement therewith in the normal fashion.

FIG. 3 is a top view of the embodiment of the cradle assembly as shown in FIG. 1.

FIG. 4 is a bottom view of the embodiment shown in FIG. 1.

Similar reference characters refer to similar parts throughout the several views of the drawings.

DETAILED DESCRIPTION

As shown in FIGS. 1 through 4, the cradle assembly of the present invention is generally indicated as 10 and includes a base means 12 having a substantially elongated, linear configuration and being rigidly attached between handle means generally indicated as 14 and the cradle means generally indicated as 16. The handle means 14 and the cradle means 16 are integrally attached to opposite ends of the base means 12 and substantially define the opposite ends of the cradle means 10.

More specifically, the cradle means 16 includes a base plate 18 interconnected between the ends of leg elements 20. The cradle means 16 comprises, preferably, two leg elements 20 which are integrally attached approximately at point 22 to the base means 12. As shown, the leg elements 20 are disposed in spaced relation to one another so as to define an aperture means 24. This aperture means is configured and disposed so as to substantially surround the end or foot portion generally indicated as 26 of the cast generally indicated as 28.

With reference to FIG. 2, the cast 28 is represented in surrounding, supportive relationship to a limb 29 and/or foot 30 in the common and conventionally accepted manner.

Support means 32 has its opposite ends 34 and 36 attached to different of said two leg elements 20 as shown in FIGS. 1, 2 and 4. By virtue of this disposition, support means 32 extends outwardly from the plane defined by the leg elements 20 as best shown in FIGS. 2 and 4. In addition, a preferred embodiment of the present invention has the support means 32 having a substantially curvilinear configuration so as to surround the correspondingly positioned portion of the casted limb as shown in FIG. 2. It should be noted that the relative dispositions between the support means 32 and the cradle means 16 is such as to both at least partially surround and support the end or foot portion 26 of the casted limb 28, again, as clearly shown in FIG. 2.

The handle means 14, is integrally attached to base means 12 at the opposite end thereof relative to the cradle means 16. The handle means includes a grasp element 39 interconnected to the base means 12 by arm members 40. Handle aperture means 42 is generally thereby defined to the relative dispositions of the grasp element 39 and arm elements 40. The configuration and dimensions of the aperture means 42 is such as to allow the hand 44 of the patient, or other person, to grasp grasp element 39 and thereby manipulate both the cradle assembly 10 and the cast 28 and limb 29 on which the cradle assembly is mounted (FIG. 2).

One or more connecting mean generally indicated as 46 may be attached along the length of the cradle assembly 10 in order to mount the cradle assembly on the cast 28 and/or limb 29 for movement therewith. More specifically, the connecting means comprises one or more strap elements 48 having one end 50 attached to the base means 12 along the length thereof. The opposite end 52 of the strap element 48 is configured to engage attachment assembly generally indicated as 54 which may be formed and/or mounted on the base means or along the length of the cradle assembly. The configuration of the end 52 of strap element 48 may be such as to allow buckling to the attachment means 54 in the conventional manner. Accordingly, a plurality of holes 55 may be provided therein.

Accordingly, insertion of the casted limb within the cradle assembly and engagement with the support means 32 provides a supportive feature to the casted limb. Attachment of one or more of the strap elements 48 will allow the cradle assembly 10 to move with the casted limb so that there is no need for reattachment and removal upon movement of the patient. Manipulation of the handle means by the hand of the patient allows for orientation of the cradle assembly and the casted limb therein due to the relative positions of the base means, handle means, support means and cradle assembly.

It will thus be seen that the objects set forth above, among those made apparent from the preceding description, are efficiently attained, and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention which, as a matter of language, might be said to fall therebetween.

Now that the invention has been described, What is claimed is:

1. A cradle assembly of the type primarily for positioning a limb disposed in a cast structure, said cradle assembly comprising base means extending in interconnecting disposition between opposite end portions of said cradle assembly, stirrup means substantially defining one end of said cradle assembly, handle means connected to said base means at the substantially opposite end of said base means relative to said stirrup means, said base means comprising a rigid shaft element disposed in integral, interconnected relation between said stirrup means and said handle means, said stirrup means comprising an aperture means, said aperture means including a predetermined dimensioned configuration, whereby said stirrup means is disposed at least partially in surrounding relation to a portion of the casted limb.

2. A cradle assembly as in claim 1 wherein said stirrup means comprises a base plate disposed in supporting relation to the casted limb.

3. A cradle assembly as in claim 2 wherein said stirrup means further comprises at least two leg elements each connected to said base plate in spaced relation to one another and connected to said base means, said leg elements disposed to at least partially define, along with said base plate, said aperture means.

4. A cradle assembly as in claim 1 further comprising support means disposed in spaced relation to said stirrup means and extending outwardly from the plane of said stirrup means.

5. A cradle assembly as in claim 4 wherein said support means comprises a substantially curvilinear configuration having opposite extremities thereof integrally connected to substantially oppositely disposed portions of said stirrup means.

6. A cradle assembly as in claim 3 wherein said cradle assembly further comprises support means including a longitudinal, substantially semi-circular configuration along the longitudinal axis thereof, said support means having its opposite extremities, each integrally connected to separate of said two leg elements.

7. A cradle assembly as in claim 1 wherein said handle means comprises at least one grasp element, handle aperture means defined within said handle means contiguous said grasp element, whereby said grasp element may be held by the hand of the user of the cradle assembly.

8. A cradle assembly as in claim 1 further comprising connecting means attached to said base means and disposed in engaging relation to the casted limb.

9. A cradle assembly as in claim 8 wherein said connecting means comprises at least one strap element attached to said base means in disposable and surrounding attached relation to the casted limb.

10. A cradle assembly as in claim 9 further comprising a plurality of strap elements attached to said cradle assembly along the length thereof and in spaced relation to one another, each of said strap elements positionable in surrounding relation to the casted limb, whereby said cradle assembly is mounted for movement with the cast.

* * * * *